United States Patent
Kimbrough et al.

(10) Patent No.: US 9,746,316 B1
(45) Date of Patent: Aug. 29, 2017

(54) HIGH-RESOLUTION IN-LINE METROLOGY FOR ROLL-TO-ROLL PROCESSING OPERATIONS

(71) Applicants: Brad Kimbrough, Tucson, AZ (US); Erik Novak, Tucson, AZ (US)

(72) Inventors: Brad Kimbrough, Tucson, AZ (US); Erik Novak, Tucson, AZ (US)

(73) Assignee: 4D TECHNOLOGY CORPORATION, Tucson, AZ (US)

( * ) Notice: Subject to any disclaimer, the term of this patent is extended or adjusted under 35 U.S.C. 154(b) by 68 days.

(21) Appl. No.: 15/049,080

(22) Filed: Feb. 21, 2016

Related U.S. Application Data

(60) Provisional application No. 62/119,730, filed on Feb. 23, 2015.

(51) Int. Cl.
*G01B 11/02* (2006.01)
*G01B 11/24* (2006.01)

(52) U.S. Cl.
CPC ................. *G01B 11/2441* (2013.01)

(58) Field of Classification Search
CPC ............ G01B 11/2441; G01B 2290/70; G01B 9/02022; G01N 21/89; G01N 21/8901; G01N 2021/8909; G01N 2021/8911
USPC .......................................... 356/431, 495, 511
See application file for complete search history.

(56) References Cited

U.S. PATENT DOCUMENTS

| | | | |
|---|---|---|---|
| 6,097,482 A * | 8/2000 | Smith | G01N 21/8901 250/237 R |
| 6,304,330 B1 | 10/2001 | Millerd et al. | |
| 6,449,048 B1 * | 9/2002 | Olszak | G01B 11/2441 356/497 |
| 6,552,808 B2 | 4/2003 | Millerd et al. | |
| 7,170,611 B2 | 1/2007 | Millerd et al. | |
| 7,298,497 B2 | 11/2007 | Millerd et al. | |
| 2005/0237535 A1 * | 10/2005 | Deck | G01B 11/2441 356/497 |
| 2011/0228116 A1 * | 9/2011 | Margalith | G01J 3/2803 348/222.1 |
| 2013/0063730 A1 * | 3/2013 | Sykora | G01B 11/2441 356/511 |
| 2015/0177155 A1 * | 6/2015 | Haran | G01J 3/42 250/341.1 |

OTHER PUBLICATIONS

James C. Wyant, "Dynamic Interterometry," Optics & Photonics News, Apr. 2003.

* cited by examiner

*Primary Examiner* — Tarifur Chowdhury
*Assistant Examiner* — Jonathon Cook
(74) *Attorney, Agent, or Firm* — Antonio R. Durando

(57) ABSTRACT

A substrate is tested with an interferometer in-line in a roll-to-roll processing operation to detect defects and exclude them from further processing. A tilt is introduced in the illumination path of the interferometer to allow detection of best fringes in a selected measurement field of view (FOV) that is smaller than the camera FOV in the direction transverse to the fringes. At each acquisition frame, the measurement FOV is shifted to track the best-fringe position within the camera field of view based on irradiance acquired at the previous step. As a result, the system is able to accommodate substrate flutter and roller runout and maintain focus on the substrate that allows precise identification of defects and their isolation for subsequent processing.

11 Claims, 7 Drawing Sheets

PROVIDE A REFERENCE SURFACE CONFORMING SUBSTANTIALLY TO THE
CURVATURE OF THE ROLLER OVER WHICH THE SUBSTRATE IS BEING TESTED

SELECT A PORTION OF THE INTERFEROMETRIC CAMERA FIELD OF VIEW TO DEFINE
THE SIZE OF THE MEASUREMENT FOV

SELECT THE INITIAL LONGITUDINAL POSITION OF THE MEASUREMENT FOV
WITHIN THE CAMERA FOV BASED ON THE EXPECTED LOCATION OF THE INITIAL
INTERFEROMETRIC BEST FRINGE SIGNAL

AT SELECTED DATA ACQUISITION STEPS FOLLOWING THE INITIAL ACQUISITION
STEP, UPDATE THE LONGITUDINAL POSITION OF THE MEASUREMENT FOV
WITHIN THE CAMERA FOV BASED ON THE BEST FRINGE-SIGNAL LOCATION
WITHIN THE CAMERA FOV ACQUIRED DURING THE PREVIOUS STEP

PROFILE THE SUBSTRATE USING ONLY DATA ACQUIRED FROM THE CURRENT
MEASUREMENT FOV

ANALYZE THE PROFILES SO GENERATED TO IDENTIFY THE LOCATIONS OF
UNACCEPTABLE DEFECTS IN THE SUBSTRATE

STOP FURTHER PROCESSING OF THE SUBSTRATE AT THE LOCATIONS SO
IDENTIFIED

FIG. 4

HIGH-RESOLUTION IN-LINE METROLOGY FOR ROLL-TO-ROLL PROCESSING OPERATIONS

RELATED APPLICATIONS

This application is based on and claims the priority of Provisional Application Ser. No. 62/119,730, filed Feb. 23, 2015, hereby incorporated by reference.

BACKGROUND OF THE INVENTION

Field of the Invention

The invention relates to optical metrology and related systems. In particular, it concerns in-line measurements of materials being processed in a roll-to-roll operation.

Description of the Prior Art

There is a need for in-line metrology for materials going through a roll-to-roll processing operation. The need exists both for raw substrates (such as for quality control of substrate materials by device manufacturers and quality measurements by the substrate manufacturers) and also for quality control of actual devices, both during and after processing for manufacture. Processing typically involves the deposition of uniform layers of material across the entire width of a plastic web substrate, or the deposition of traces, transistors, or other features, to create electronic circuits on flexible plastic substrates in an increasing number of applications, including displays, biomedical devices, smart apparel, and advanced sensors. Such flexible webs may be up to one meter in width and move at speeds greater than one meter per minute; therefore, real-time measurements of web features are difficult to carry out.

In order to achieve effective quality control during such processing, 3D metrology is essential because several major failure modes of plastic electronic devices are associated with parameters that require precise height measurements. Roughness has been found to be a major contributor to transistor failure in flexible circuits; therefore, it needs to be tightly measured and controlled. While very smooth substrates exist, they are very expensive. Thus, manufacturers often utilize lower-quality materials and either coat them to smooth them out, or measure the roughness and exclude very rough areas from further processing.

Regardless of quality, all plastic substrates unavoidably carry some defect within them. The slope of those defects can cause cracking—for example, if a conductive trace, transistor, or other element is deposited across a highly sloped feature, it is very likely to crack. However, if the defect is shallow, it is not usually a problem and there is no need to exclude it from further processing. Thus, 2D measurements of defects do not provide sufficient information for good quality-control decisions by manufacturers about whether or not to include the defect in the product area. Because of its high vertical and transverse resolution, large field-of-view, extremely fast measurement times, and nanometer precision, 3D optical metrology is particularly suited for in-situ roll-to-roll measurement of the height and slope of such defects in real time during the deposition process.

Existing interferometric inspection tools measure only small-areas and are suitable mainly for laboratory-bench work. With a typical lateral resolution of about 2 µm, such systems can measure areas less than 1 square mm in the span of several seconds, while also requiring vibration isolation. Current in-line methods are machine-vision-based with limited lateral resolution (~100 µm) and often are incapable of measuring roughness or quantifying heights of defects. In addition, when testing transparent substrates, such in-line techniques often also suffer from reflections from the back side of the film, which may be only 25 µm thick, or from the roller mechanisms over which the film is traveling. In order to measure surface roughness in the range of 1 nm rms, the metrology tool must have micrometer-level lateral resolution and be capable of measuring flexible samples despite effects that can vary the position of the substrate relative to the tool.

Thus, any in-line metrology solution must deal with several major challenges. The first is that the substrate material, being flexible, flutters as it travels across rollers. This means that it moves up and down in relation to the roller, thus going in and out of focus of a stationary optical system that is looking at it. Because of this problem, in order to account for this flutter problem, existing metrology systems typically look at the substrate while in continuous contact with the substrate. This is very helpful, but it does not entirely solve the problem because of the potential damage to the substrate due to its contact with the measurement system while in motion over the roller.

Another challenge lies in the rollers themselves. They inherently have some amount of runout; that is, the amount by which the top of a roller will move up and down during a rotation around its axis. A typical runout is on the order of tens to hundreds of micrometers. Therefore, if an optical instrument is focused on the top of the roller, any significant amount of runout will also cause the optical image to be out of focus. Both web/substrate flutter and roller runout mean not only that a certain amount of focus variation must be tolerated by the optical system, but also that it be vibration-immune to avoid errors caused by the motion of the web and/or the roller, as well as by the overall machine vibration due to vacuum pumps, multiple motors, and other mechanical devices used in the production of flexible circuits.

Furthermore, because in-line optical metrology systems on roll-to-roll operations typically image onto the web while is passes by on the roller, the curvature of the roller means that there is a focal distance variation across the field of view of the objective (for example, if the metrology system is focused on the top of the roller, with the top in the center of the field of view, the edges will be slightly out of focus due to the roller's curvature). In view of the foregoing, any in-line instrument must account for web flutter and roller runout, it must be substantially vibration-immune, and it must account for the curvature of the rollers. Additionally, end users often require that the optical system contain minimal moving parts, so as to minimize incidents of failure. Finally, many stages of existing optical systems, such as those used for focusing, utilize vacuum-compatible components that are undesirable because of their cost. Therefore, a 3D optical system that overcame these problems would represent a valuable step forward in the art. This invention is directed at providing such a system.

SUMMARY OF THE INVENTION

The invention lies in the ideas of tilting the interferometer measuring a flexible substrate to identify defects in-line in a roll-to-roll operation so as to reduce the width of the fringes recorded within the field of view of the camera of the interferometer. As a result, only a portion of the entire field of view, referred to herein as the measurement field of view, is required to obtain meaningful metrology information from maximum-contrast fringes detected within it. Because perturbations of the position of the substrate around the focal point of the illumination path of the interferometer as a result of flutter or runout cause a shift in the position of the best fringes in the camera field of view, the measurement field of view is shifted within the camera field of view at each data acquisition step to track the position of the currently identified best fringes. As a result, the computational time is greatly reduced and the substrate can be tested in-line in real time with a degree of precision that enables the immediate identification of unacceptable substrate defects and their location on the substrate, thus making it possible to stop further deposition processing on those locations without interruption of the roll-to-roll operation.

In the preferred embodiment of the invention, the reference surface of the interferometer is selected with a curvature that conforms to the shape of the roller over which the measurements are carried put. While not essential, this feature is particularly useful with rollers of smaller diameter, such as 100 mm or less.

Using conventional techniques and system components, the steps of the invention involve selecting a portion of the field of view of the interferometer's camera to define the size of a measurement field of view (FOV) within the longitudinal direction of the camera FOV; tilting the interferometer along the direction of substrate travel to reduce their width so as to enable detection of best-fringe signals within the measurement FOV; selecting the initial longitudinal position of the measurement FOV within the camera FOV based on the expected location of the initial interferometric best-fringe signal (preferably by adjusting the interferometer so that it is focused at the center of the camera FOV); beginning the acquisition of fringe data detected by the camera during successive data acquisition steps; and, at each acquisition step following the initial acquisition step, updating the longitudinal position of the measurement FOV within the camera FOV based on the best-fringe-signal location within the camera FOV acquired during the previous step; and, at each data acquisition step, profiling the substrate with high-resolution metrology techniques using only data acquired from the current measurement FOV. As a result of this approach, defects and their locations in the substrate can be identified and further processing of the substrate at such locations may be interrupted while continuing the roll-to-roll processing of the rest of the substrate.

Various other advantages will become clear from the description of the invention in the specification that follows and from the novel features particularly pointed out in the appended claims. Therefore, this invention includes the features hereinafter illustrated in the drawings, fully described in the detailed description of the preferred embodiments and particularly pointed out in the claims, but such drawings and description disclose only some of the various ways in which the invention may be practiced.

BRIEF DESCRIPTION OF THE DRAWINGS

FIG. 4 is a flow-chart of the steps involved in the preferred embodiment of the invention.

DETAILED DESCRIPTION OF THE PREFERRED EMBODIMENT

As used in the art, the term "FOV" is used herein to refer to the field of view of the optics of the interferometer measuring a test substrate according to the invention. FOV is also used with reference to the detector pixels corresponding to the field of view imaged by the interferometer. The term "OPD" refers to the optical path difference between interfering light beams, as conventionally used in interferometry. The terms "detector" and "camera" are used interchangeably to refer to any sensor used to record light irradiance received from an interferometric instrument. The terms "objective" and "interferometer" are also used interchangeably when referring to interferometers that include an objective as a distinct component thereof, as opposed to interferometers with integrated optics that focus the illumination beam on the test sample. With reference to the field of view of the interferometer camera used to practice the invention, the term "longitudinal" is used to denote the direction along which the substrate being tested moves on the roller transporting it and the corresponding direction in the field of view; that is, the direction perpendicular to the fringes produced by the measurement. The terms "web" and "substrate" are used interchangeably to refer to the sample material being tested in-line in a roll-to-roll processing operation. The term "measurement FOV" is used to define the pixel size of the area within the camera FOV that is used for acquiring interferometric data at each step of the procedure of the invention, it being understood that the location of the measurement FOV is not fixed but is shifted longitudinally within the camera FOV as required to carry out the invention. The above definitions are all intended to apply to the description of the invention as well as to the claims that follow.

The present invention is based on so-called dynamic interferometry, which in the art has become known to represent a high-speed, vibration-immune, 3D metrology founded on both spatial-carrier techniques and polarization techniques (implemented with pixellated masks or beam-splitters). (See James C. Wyant, "Dynamic Interferometry," Optics & Photonics News, April 2003, herein incorporated by reference.) In particular, we found that spatial-carrier techniques such as described in copending Ser. No. 13/421,832 and polarization/pixellated-mask techniques such as described in U.S. Pat. No. 6,304,330, U.S. Pat. No. 6,552,808, U.S. Pat. No. 7,170,611 and U.S. Pat. No. 7,298,497 (all hereby also incorporated by reference) may be used advantageously for in-line dynamic interferometry of flexible electronic components.

Figure 1:
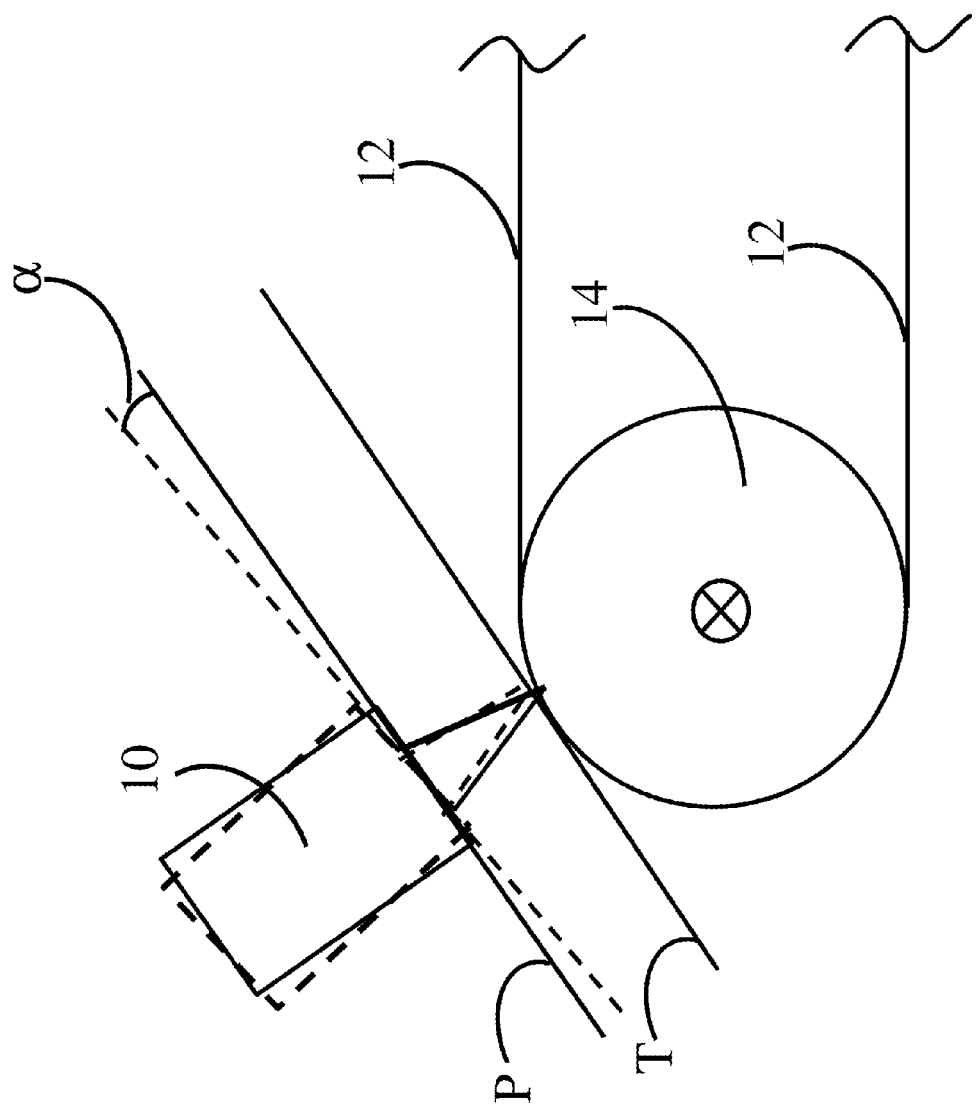
FIG. 1 is a schematic illustration of a roll-to-roll web processing apparatus showing quality-control in-line interferometric testing with an instrument focused on a substrate traveling on a roller.
Figure 2:
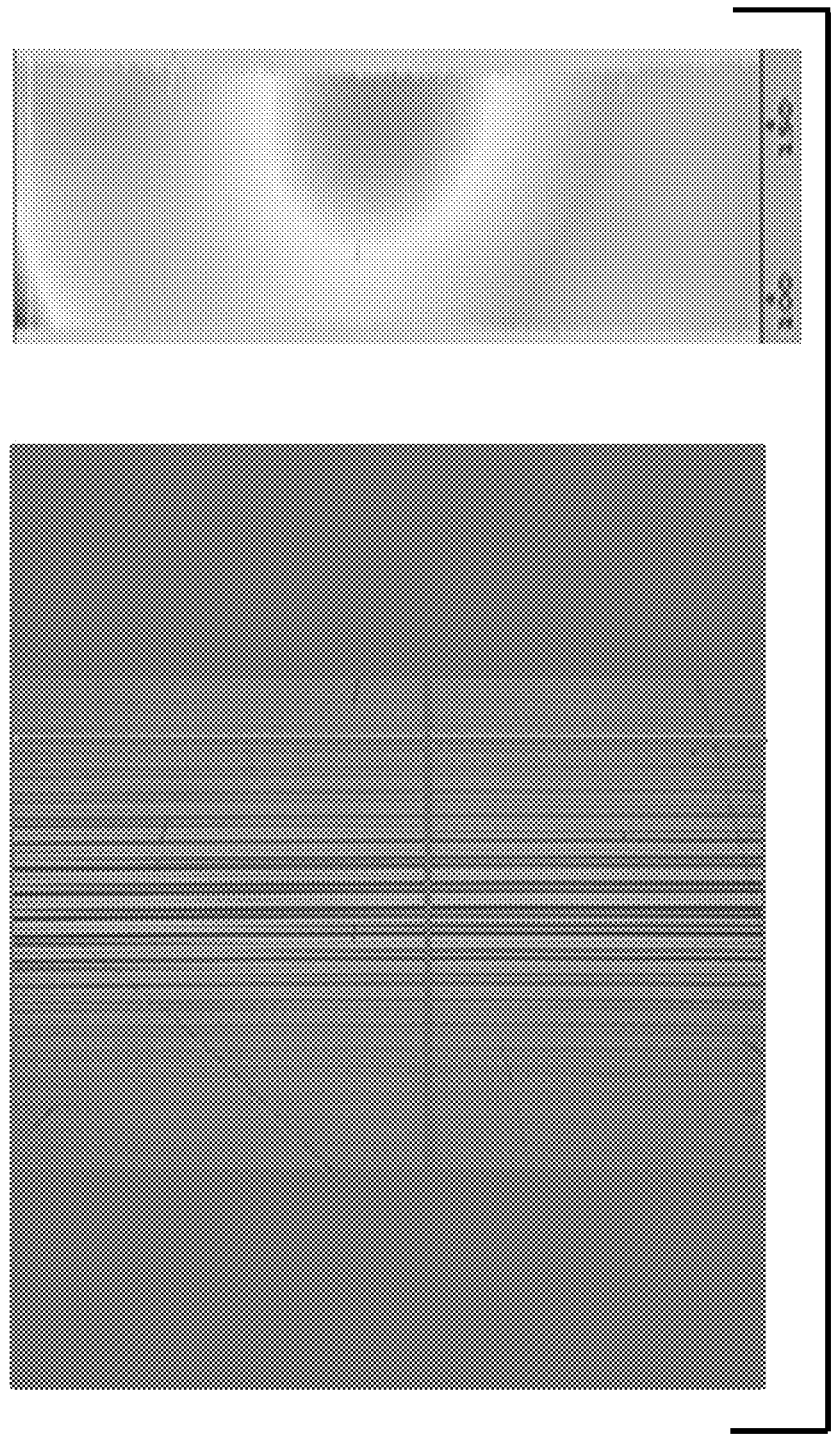
FIG. 2 illustrates narrowly localized fringes within the camera field of view as a result of longitudinal tilt applied to the interferometer with respect to the substrate being measured (on the left) and the corresponding height map (on the right).

According to the invention, two innovative elements are introduced in the normal practice of dynamic interferometry to render it most valuable for in-line roll-to-roll measurements of flexible substrates. First, an essential step in order to achieve immunity to focus variations from web flutter and roller runout, tilt is introduced in the direction of roll-to-roll travel (longitudinal direction) between the interferometer and the substrate being measured, as shown schematically in FIG. 1. The purpose of such tilt is to reduce the width of the fringes and the amount of tilt is selected so as to enable the interferometric camera to record the best fringes (i.e., the fringes with maximum irradiance signal) within a relatively small longitudinal portion of the camera's field of view (as seen in FIG. 2, for example). The interferometer 10 is preferably positioned so as to measure the moving substrate 12 at a location where the substrate is in full contact with the roller 14 over which it travels. As illustrated schematically in two dimensions and in exaggerated fashion in the figure, a tilt a is introduced between the plane P of the interferometer 10 (i.e., the plane from which its illumination path emanates in the direction of the substrate) and the plane T tangent to the roller 14 at the location over which the illumination path of the interferometer is focused. For spatial carrier techniques, this can be the same tilt as is optimally required for measurements (i. e, a tilt producing a ¼ fringe per detector pixel). For pixellated-mask techniques, it could be the same tilt or a different one (such as smaller, if desired). The critical feature for the invention is that a judiciously selected tilt be introduced, as one skilled in the art would know, so that fringes are sufficiently narrow to allow the best fringes to be recorded in a relatively small longitudinal portion of the camera's field of view.

Figure 3:
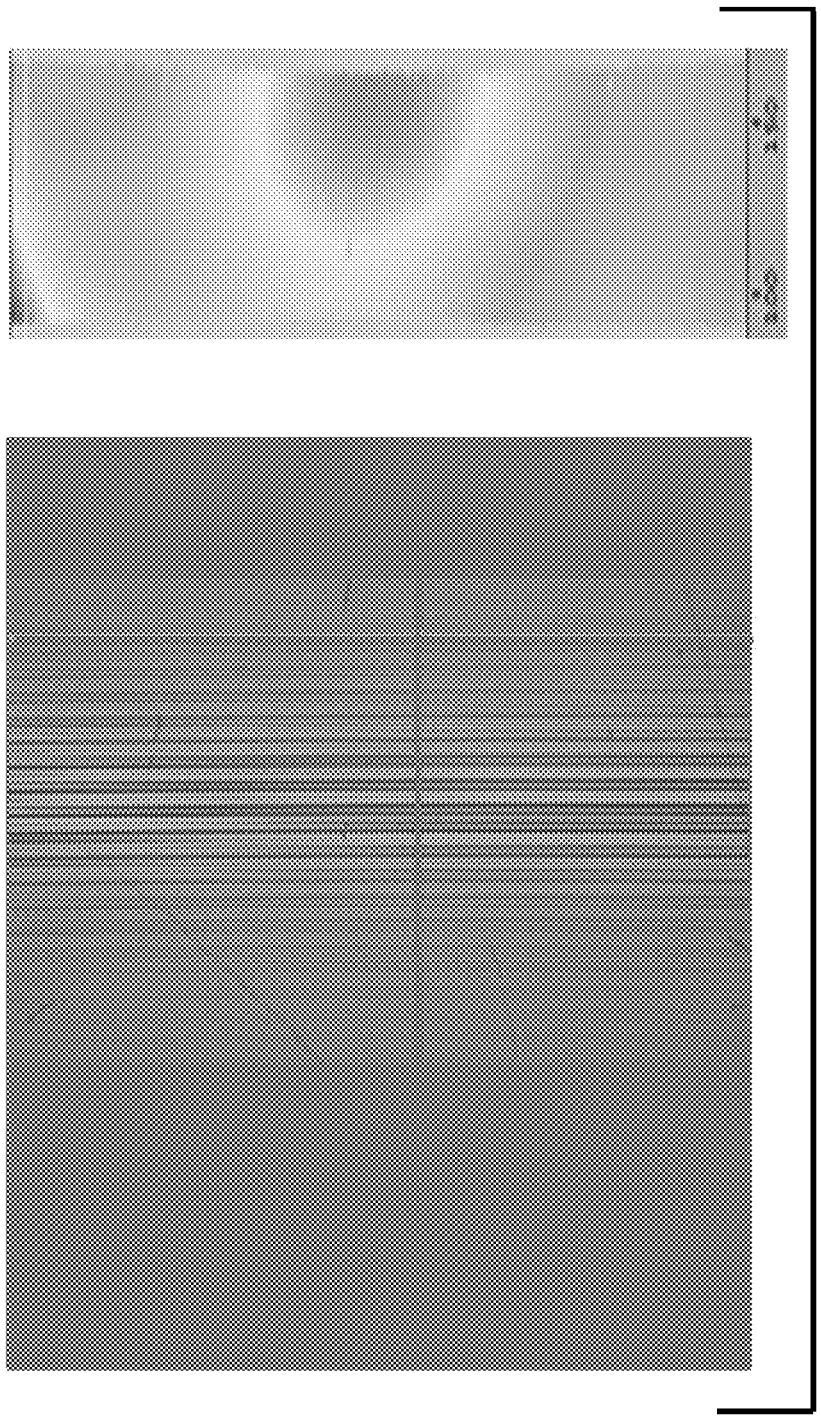
FIG. 3 illustrates the longitudinal shift of localized fringes within the camera field of view resulting from the effects of flutter and/or runout.

With the introduction of such a tilt, the fringes are localized within the camera's field of view, as illustrated in the image of FIG. 2 where the vertical direction shows the interference irradiance acquired along the width of the roller and the horizontal direction shows the irradiance along the direction of travel of the sample (the longitudinal direction). FIG. 2 shows that the best fringes occupy only a relatively small portion of the field of view in the direction of substrate travel. Therefore, according to the invention, only data with fringes within such a selected portion of the field of view are processed to produce 3D height information. Because the usable signal for interferometry only occupies a fraction of the camera pixels in the longitudinal direction (about ⅕, for example), the rest of the field of view remains open to show shifts of the best fringes as a result of changes in the relative distance between the interferometer and the moving substrate. That is, as the substrate goes in and out of focus due to flutter or runout, the best interference fringes will move left or right across the field of view of the camera (as illustrated in FIG. 3, for example). Therefore, according to the invention, this feature is used advantageously to enable the in-line measurement of substrates during roll-to-roll processing operations, or at least greatly reduce measurement errors caused by substrate flutter and roller runout.

In operation, the fringes (i.e., the strength of the interference signals across the detector) are processed in conventional manner to find and record the location of maximum signal, according to a predetermined threshold, along the direction of substrate travel in the field of view (i.e., the horizontal direction in FIG. 2). For the purposes of the invention, the size of a fraction of the detector's entire FOV (for example, ⅕, such as an area of 200×200 pixels of a 1000×1000-pixel camera) is selected for the purpose of tracking the shifts of the best fringes and the corresponding height calculations during in-line measurement of a substrate. Such selected area is hereinafter called "measurement FOV" for convenience. It is understood that the measurement FOV will shift within the overall field of view of the camera according to the movement of the substrate above and below the focal distance of the optics of the interferometer. Accordingly, the phase calculation for profiling the substrate at each data frame is limited to the fringes corresponding to the measurement FOV. That is, at each data processing step the phase calculation is based only on data within the measurement FOV, which at each step will correspond to the region of maximum interference signal (according to a judiciously selected threshold). As a result, the effects of flutter and runout on the focal position of the substrate are essentially eliminated because the measurement FOV will always correspond substantially to the best in-focus position of the substrate.

For instance, the interferometric instrument can be set up initially by adjusting focus so that the best signal is perfectly centered on the camera. Using ⅕ of a camera with 1000 longitudinal pixels, for instance, would mean that the best fringes are assumed (correctly, because of the focal adjustment) to be centered at pixel 500 and only a stripe of data from longitudinal pixels 400 to 600 (the initial measurement FOV) would be utilized initially to calculate phase. (Note that only camera pixels corresponding to the longitudinal direction of travel of the substrate are referenced, for simplicity.) At each subsequent step of data acquisition, a sufficient number of pixels along the longitudinal direction of the entire field of view is processed to find the longitudinal location of maximum contrast (or some other measure of best fringes). For example, if the substrate or the roller moved up or down, the second frame might for instance have the maximum signal centered at pixel 550 instead of 500. Thus, for the $3^{rd}$ frame, pixels 450 to 650 would be used for the location of the measurement FOV. In actuality, maybe the current maximum-contrast measurement from the $3^{rd}$ frame shows that in fact the best fringes were at pixel 555, in which case the $4^{th}$ frame would use pixels 455 to 655, and so on. In other words, at each data acquisition frame, the best signal location from the last frame is used to locate the measurement FOV within the camera's overall FOV and data registered at such current measurement FOV are used to calculate phase. Concurrently, at each acquisition frame, the longitudinal location of best fringes is determined by processing selected longitudinal pixels over the entire camera FOV and the result is fed forward for the next frame. (Note, however, that this step could be carried out only at selected acquisition steps, rather than at each step—for instance, at every other frame.) Having enough camera pixels to allow sufficient focus variation, the full +/−25 um typical web flutter and the runout of a precision roller can thus be accommodated. Note that only a few rows of camera pixels have been described for finding the longitudinal location of maximum contrast at each step of the procedure. This is so because of the current processing limitations for the computational requirements of the invention for in-line operation. However, it is understood that more rows, up to the entire camera FOV, could be used as improvements in processing speeds become available.

Another aspect of the invention is not critical but it is particularly important for small-radius rollers. As mentioned, when an interferometer is focused on a roller (i.e., a web wrapper around it), part of the roller within the field of view will be out of focus because of the curvature of its cylindrical surface. Therefore, if a flat reference surface is used for the interferometric measurement, the fringes not only shift laterally within the field of view with the movement of the substrate, but the fringe density also changes greatly with the varying position of the zero-OPD location within the camera field of view. For example, the zero-OPD location on the cylinder may be centered in the field of view with a given fringe density in one frame and be shifted to the right or left with a different fringe density in the next frame as a result of having a flat reference surface while measuring a curved surface. This change in fringe density can affect the measurement results, especially for spatial-carrier processing techniques. Therefore, the use of a cylindrical reference surface that matches the diameter of the roller carrying the substrate under test will substantially reduce any error caused by fringe-density variations. Thus, the use of a reference surface having the shape and orientation of the roller is preferred.

In view of the foregoing, the preferred embodiment of the invention involves the combination of novel processing steps as well as the use of a reference surface that conforms to the curvature of the roller of the equipment over which the substrate under test travels as well as the introduction of a tilt in the measurement interferometer in the direction of travel. The processing steps involve selecting a portion of the camera field of view in the direction transverse to the fringes to define the contiguous-pixel size of the measurement FOV for in-line interferometric processing; initializing the data acquisition process by electing a longitudinal position for the measurement FOV within the camera FOV; at each data acquisition step, acquiring interferometric irradiance signals within the current measurement FOV and calculating a corresponding sample-substrate height map in conventional manner, acquiring interferometric irradiance signals along predetermined longitudinal pixels of the camera FOV and calculating a corresponding location of best fringes in conventional manner; and updating the position of the measurement FOV within the camera field of view at each data acquisition step by using the location of maximum signal strength recorded in the previous step. The height measurements so acquired are then analyzed according to some predetermined pass/fail standard to identify unacceptable defects and their locations in the measured substrate. Further deposition or other processing of the locations corresponding to such unacceptable defects can then be interrupted during the in-line operation. The procedure is outlined in FIG. 4.

Figure 5:
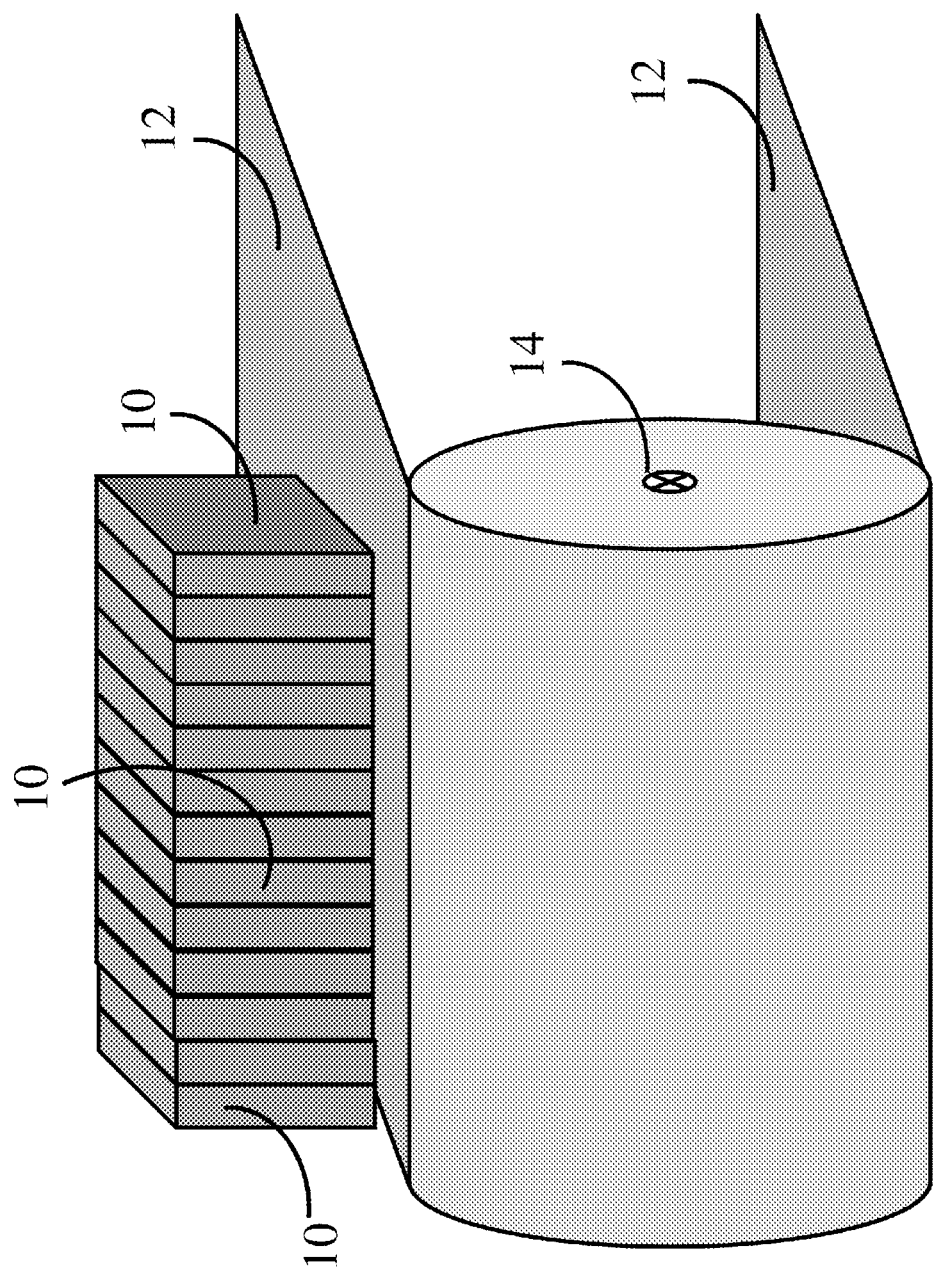
FIG. 5 illustrates an array of interferometers mounted across the width of a substrate being measured in real time during processing in a roll-to-roll operation.

Inasmuch as current roll-to-roll equipment processes webs as much as one meter wide, it is understood that several adjacent interferometric modules need to be assembled across the web for in-line processing with total surface coverage. Using a 5 megapixel commercial CMOS camera with 2 μm pixels, a super-bright LED source, small optics and a unique housing designed for this purpose, a miniature interferometer (FlexCam™, by 4D Technology Corporation of Tucson, Ariz.) was produced that is capable of performing dynamic phase-shifting interferometry in a single camera frame. FIG. 5 illustrates multiple modules 20 mounted over the web 12 on a roller 14 of a winder/rewinder machine, such as typically used to transfer material from one roller to another (for instance, to put material on a roller of the proper diameter for additional processing). The overall dimensions for each module are approximately 75 mm×90 mm×15 mm. In order for an array of such modules to be practical, all interference calculations and analyses are done on-board using both a microcomputer and graphics processing chip. In normal use, only the relevant defect and roughness parameters are transmitted to a host computer via a single Ethernet cable. This keeps costs low and vastly simplifies creating an array of modules for large area coverage.

In order to ensure immunity to stray reflections when testing a transparent substrate, the module 20 uses a low-coherence LED with approximately 30 nm bandwidth so that interference fringes are generated only by the surface under test, which may be the top or bottom surface of the flexible substrate. According to the invention, the area over which interferograms are analyzed at each step (the measurement FOV) tracks where the signal is localized, giving the unit more than +/−30 μm depth of focus, which is larger than required by precision metrology rollers. This limits the overall field of view of the module to only 0.6 mm in the longitudinal machine direction (along the film direction of travel) but maintains a 4 mm field of view in the transverse direction (across the film). With rapid on-board processing capable of operating in excess of 30 frames/second, 100% coverage is still obtained in the machine direction, so sampling is not compromised.

Figure 6:
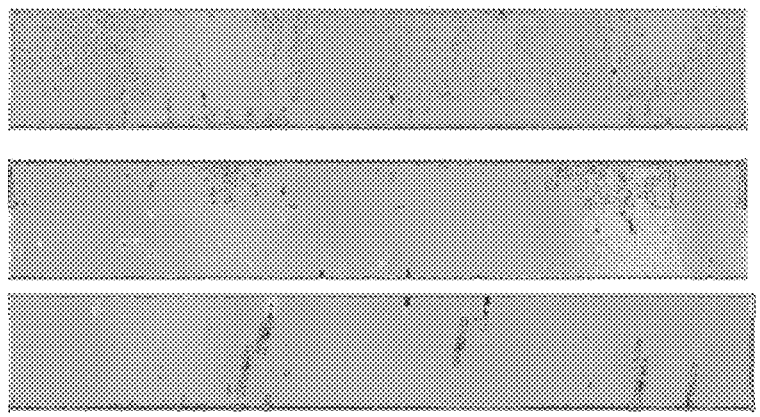
FIG. 6 shows images of the results produced by an interferometric module developed for the invention from static tests of films with 2-8 µm defects (top), 5-12 µm effects (middle), and 10-30 µm defects (bottom).

A variety of tests were performed to validate the performance of the FlexCam™ module in measuring flexible electronics substrates. First, height accuracy was verified using a glass VLSI step standard certified as 90.8 nm+/−0.2 nm in height. The module was found to measure the height within the uncertainty of the standard. Next, a variety of known defect sizes were measured to ensure the lateral resolution of the system was adequate for industry needs. Known inclusions are sometimes added to plastic packaging films to control their adhesion properties, so several custom samples were acquired for use in the validation of the module's metrology properties. FIG. 6 shows the results of measurements of films with 2-8 μm defects, 5-12 μm defects, and 15-30 μm defects (respectively, from top to bottom). All classes of defects were successfully detected and measured with no surface calculation errors. These films were approximately 50 μm thick and no effect was seen from the back side of the film or from the surface underneath the film.

Figure 7:
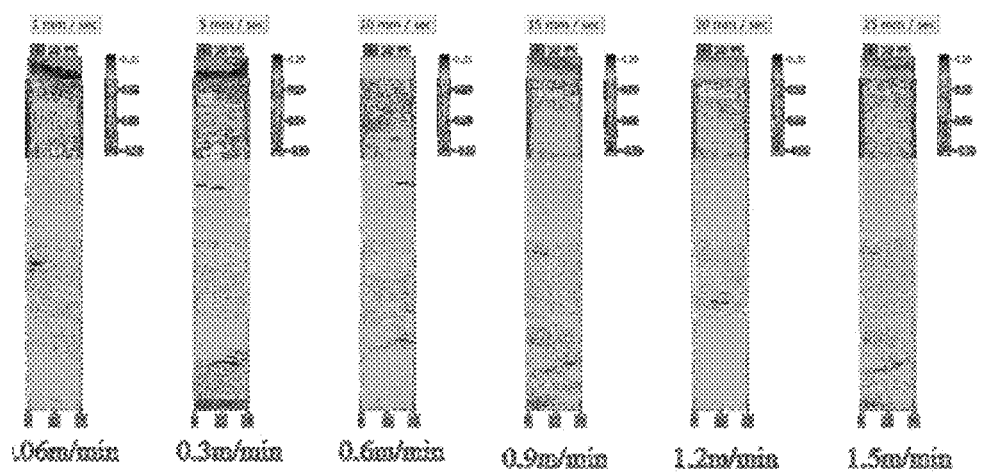
FIG. 7 shows images of the results produced by the same interferometric module of FIG. 6 from measurements of a PET web moving at speeds from 0.06 m/min to 1.5 m/min, which show no degradation in the quality of the results.

The FlexCam™ module was then tested to validate its metrology precision with a moving substrate. The images shown in FIG. 7 represent the results of measurements taken on a substrate mounted to an XY stage that was actuated at six different speeds. Speeds up to 1.5 m/min did not adversely affect the ability of the module to measure features or raise the noise floor above 5 nm rms. Because multiple passes across the same film area were made during speed tests, some features can be seen in multiple measurements in the images shown in the figure. However, it is noted that the features retain the same shape and height profiles regardless of web speed.

After these results were obtained in laboratory tests, the system was deployed at the Center for Advanced Microelectronics Manufacturing (CAMM) in Binghamton, N.Y. There the system was tested with a substrate in a true roll-to-roll setup. Focus variations of up to +/−30 μm were tolerated, which is greater than the +/−25 μm typical runout specification of a precision roller. Web speeds of over 1 m/minute were found to be acceptable and overall throughput for a single module was shown to be more than 17 cm$^2$ per minute. In contrast, with 2 μm pixel spacing a 3D microscope can achieve about 0.08 cm$^2$ per minute. Thus, a single module provides more than 200 times the measurement capability of such a system, and arrays can readily achieve thousands of times more areal metrology than was previously possible.

While the invention has been shown and described herein with reference to what are believed to be the most practical embodiments, it is recognized that departures can be made within the scope of the invention. Therefore, the invention is not to be limited to the details disclosed herein but is to be accorded the full scope of equivalent articles.

The invention claimed is:

1. A method of testing a substrate for defects in-line while traveling on a roller in a roll-to-roll processing operation, the method comprising the following steps:
   providing an interferometer including a reference surface and a camera, said interferometer having an illumination path directed to said substrate;
   selecting a portion of a field of view of said camera to define a size of a measurement field of view (FOV) in a longitudinal direction of the camera FOV;
   tilting the interferometer along a direction of substrate travel so as to enable detection of best-fringe signals within said measurement FOV;
   selecting an initial longitudinal position of the measurement FOV within the camera FOV based on an expected location of an initial interferometric best-fringe signal;
   beginning acquisition of fringe data detected by the camera during successive data acquisition steps;
   at selected acquisition steps following an initial acquisition step, updating a longitudinal position of the measurement FOV within the camera FOV based on a best-fringe-signal location within the camera FOV acquired during a previous step;
   profiling the substrate using data acquired from a current measurement FOV;
   analyzing profiles so generated to identify locations of defects in the substrate; and
   stopping further processing of the substrate at said locations of defects in the substrate.

2. The method of claim 1, wherein said updating step is carried out at each acquisition step.

3. The method of claim 2, wherein said reference surface conforms substantially to a curvature of said a roller in the roll-to-roll processing operation.

4. The method of claim 2, wherein said step of selecting an initial longitudinal position of the measurement FOV within the camera FOV is carried out by adjusting the interferometer so as to focus on a center of the camera FOV.

5. The method of claim 2, wherein said step of updating the longitudinal position of the measurement FOV within the camera FOV is carried out based on irradiance signals acquired from a plurality of longitudinal pixel rows of the camera FOV during the previous step.

6. The method of claim 2, wherein said updating step is carried out at each acquisition step; said reference surface conforms substantially to a curvature of said a roller in the roll-to-roll processing operation; said step of selecting an initial longitudinal position of the measurement FOV within the camera FOV is carried out by adjusting the objective so as to focus on a center of the camera FOV; and said step of updating the longitudinal position of the measurement FOV within the camera FOV is carried out based on irradiance signals acquired from a plurality of longitudinal pixel rows of the camera FOV during the previous step.

7. The method of claim 1, wherein said interferometer is a spatial-carrier interferometer.

8. The method of claim 1, wherein said interferometer is a polarization interferometer.

9. A method of testing a substrate for defects in-line while traveling on a roller in a roll-to-roll processing operation, the method comprising the following steps:
   providing an interferometer including a reference surface and a camera, said interferometer having an illumination path directed to said substrate, and said reference surface conforming substantially to a curvature of said a roller in the roll-to-roll processing operation;
   selecting a portion of a field of view of said camera to define a size of a measurement field of view (FOV) in a longitudinal direction of the camera FOV;
   tilting the interferometer along a direction of substrate travel so as to enable detection of best-fringe signals within said measurement FOV;
   selecting an initial longitudinal position of the measurement FOV within the camera FOV by adjusting the interferometer so as to focus on a center of the camera FOV;
   beginning acquisition of fringe data detected by the camera during successive data acquisition steps;
   at each acquisition step following an initial acquisition step, updating a longitudinal position of the measurement FOV within the camera FOV based on irradiance signals acquired from a plurality of longitudinal pixel rows of the camera FOV during a previous step;
   at each data acquisition step, profiling the substrate using data acquired from a current measurement FOV;
   analyzing profiles so generated to identify locations of defects in the substrate; and
   stopping further processing of the substrate at said locations of defects in the substrate.

10. The method of claim 9, wherein said interferometer is a spatial-carrier interferometer.

11. The method of claim 9, wherein said interferometer is a polarization interferometer.

* * * * *